Oct. 23, 1962 MARIE LOUISE MEILLAND NEE PAOLINO ROSE PLANT Plant Pat. 2,186
Filed May 15, 1961 2 Sheets-Sheet 1
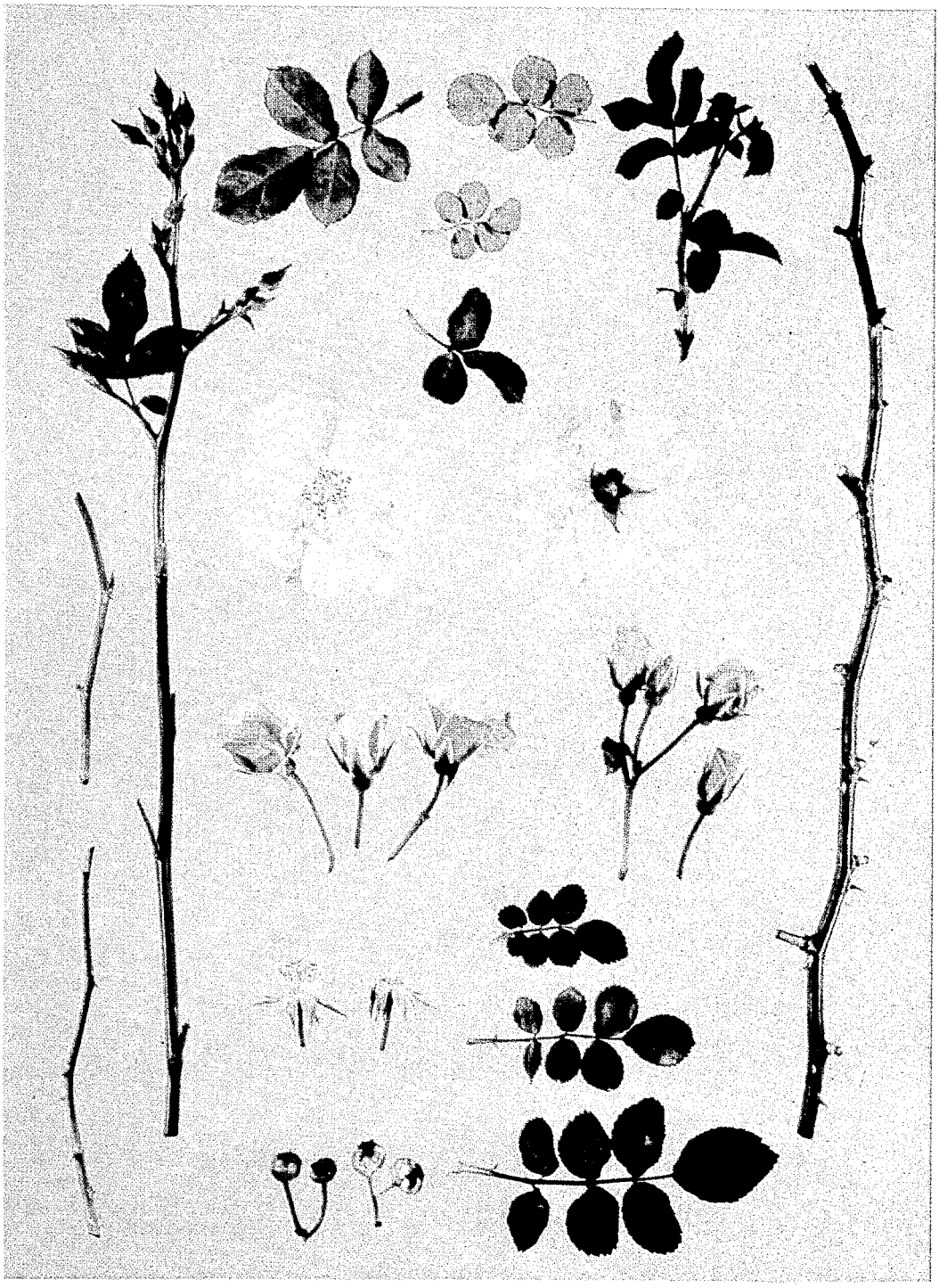
INVENTOR
Marie Louise Meilland (née Paolino)
BY Robb & Robb
ATTORNEYS

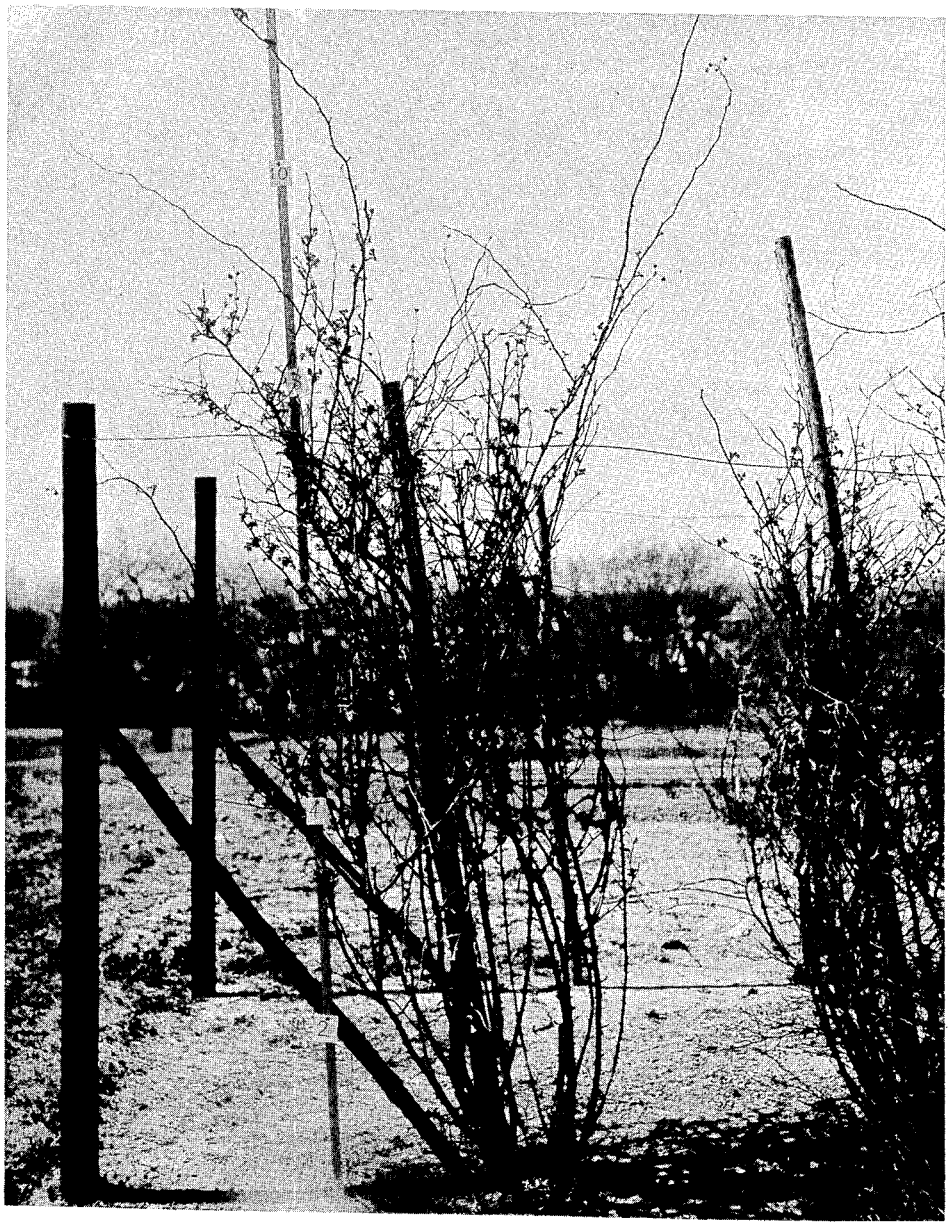
INVENTOR
Marie Louise Meilland
(née Paolino)
BY Robb & Robb
ATTORNEYS

United States Patent Office

Plant Pat. 2,186
Patented Oct. 23, 1962

2,186
ROSE PLANT

Marie Louise Meilland, née Paolino, Alpes Maritimes, France, assignor to The Conard-Pyle Company, West Grove, Pa., a corporation of Pennsylvania Filed May 15, 1961, Ser. No. 120,823
Claims priority, application France May 31, 1960
1 Claim. (Cl. 47—61)

The present invention relates to a new and distinct variety of rose plant of the climber class, which was originated by me by crossing the variety "Fashion" (U.S. Plant Patent No. 789) with an unnamed and unpatented seedling derived from crossing an unnamed and unpatented seedling of "Kordes' Sondermeldung" (known in the United States as "Independence," U.S. Plant Patent No. 1,036) × "Orange Triumph" (unpatented) with "Phyllis Bide" (unpatented).

The primary objective of this breeding was to produce a new rose variety of the everblooming climber class in which there is combined the flower characteristics of the parent variety "Fashion," with the climbing habit and vigor of the unnamed seedling parent. This objective was fully achieved, along with other desirable improvements, as evidenced by the following unique combination of characteristics which are outstanding in the new variety and which distinguish it from its parents, as well as from all other varieties of which I am aware:

(1) A hardiness much superior to the average for everblooming roses in the middle Atlantic geographical area of the United States, as evidenced by survival of the new variety without injury over the unusually severe winters of 1959, 1960 and 1961, at West Grove, Pennsylvania, U.S.A., while in the same locality and grown under the same conditions, other representative varieties of the same class, to name only a few, were damaged as follows:

"Morning Dawn" (U.S. Plant Patent No. 1,447)—canes killed back to ¼ of their total length "Gladiator" (U.S. Plant Patent No. 1,524)—injuries to extremities of canes "Coral Dawn" (U.S. Plant Patent No. 1,117)—canes killed back to ¼ of their total length "Golden Showers" (U.S. Plant Patent No. 1,557)—injuries to extremities of canes "Climbing Peace" (U.S. Plant Patent No. 932)—all canes injured moderately severely;

(2) Excellent floriferousness;

(3) An exceptional remontance for a rose of the climber class, as evidenced by comparison of the new variety with the same varieties, among others, as listed in item (1) above, and all grown in the same locality under the same conditions, with the new variety showing even greater floriferousness and greater remontance to a marked degree than the variety "Golden Showers" which repeats the blooms more freely than all others of this comparative group;

(4) Good self-cleaning characteristics as evidenced by the fact that the flower petals drop off cleanly before they become unsightly with age; and (5) A general color tonality of the flowers corresponding to Rhodamine Pink.

Asexual reproduction of my new variety by budding, as performed at West Grove, Pennsylvania, U.S.A., and also in France, shows that the foregoing characteristics and distinctions come true to form and are established and transmitted through succeeding propagations.

The accompanying drawings show typical specimens of the vegetative growth and flowers of my new variety in different steps of development and as depicted in color, as well as a separate view of a complete plant as depicted in black and white to illustrate its climbing habit of growth.

The following is a detailed description of my new variety, with color terminology in accordance with the Horticultural Color Chart of the Royal Horticultural Society, except where general color terms of ordinary dictionary significance are obvious:

Type: Hardy; climber; seedling; for garden decoration.
Class: Climber.
Breeding: Seedling.
*Seed parent.*—"Fashion."
*Pollen parent.*—An unnamed seedling derived from crossing an unnamed seedling of "Kordes' Sondermeldung" (Independence) × "Orange Triumph" with "Phyllis Bide."
Propagation: Holds its distinguishing characteristics through succeeding propagations by budding.

*Flower*

Locality where grown and observed: West Grove, Pennsylvania, U.S.A.
Flowers Borne: Several to stem; in regular rounded cluster; on stems of medium length and normal strength.
Quantity of bloom: Abundant, outdoors.
Continuity: Continuous.
Fragrance: Moderate. Nature—sweetbrier.
Bud:
*Peduncle.*—Medium length; medium caliper; stiff; almost smooth; with medium number of red hairs. Color—Lettuce Green, Plate 861/3.
*Before calyx breaks.*—Size—medium. Form—medium length; pointed; with a conspicuous neck; without foliaceous appendages on the surface of the bud; without foliaceous parts extending beyond the tip of the bud.
*As calyx breaks.*—Color—Claret Rose, Plate 021.
*As first petal opens.*—Size—medium. Form—medium length; ovoid. Color: outside—Delft Rose, Plate 020/1; inside—near Rhodonite Red, Plate 0022/1, sometimes blotched with Rhodonite Red, Plate 0022.
*Opening.*—Opens up well.
Bloom:
*Size (when fully open).*—Medium; from 2 inches to 3 inches.
*Petalage.*—Semi-double (2 or sometimes 3 rows); from 12 to 18 petals; arranged regularly.
*Form.*—Cupped at first, but becoming flat; petals being at first tightly rolled inward but later becoming loosely cupped at maturity.
Petals: Medium thickness; with both inside and outside satiny. Shape: outer—obovate; intermediate—obovate; inner—obovate.

This description of a newly opened flower was made from a rose grown outdoors in the month of September at West Grove, Pennsylvania, U.S.A.:

*Color.*—Outer petal: outside surface—Phlox Pink, Plate 625/1, shading to Phlox Pink, Plate 625/2, with a slight trace of Sulphur Yellow, Plate 1/1 at base; inside surface—Phlox Pink, Plate 625/2, shading to Phlox Pink, Plate 625/3, with small area of Sulphur Yellow Plate 1/2 at base. Inner petal: outside surface—Rhodamine Pink, Plate 527/2 at outer edge, shading to Rhodamine Pink, Plate 527/1 towards center, with blotches of Rhodamine Pink, Plate 527, and with basal quarter of petal Sulphur Yellow, Plate 1/2; inside surface—Rhodamine Pink, Plate 527/3 over all, irregularly washed with Rhodamine Pink, Plate 527/1, and with small area of Sulphur Yellow, Plate 1/2 at base.

This description was made from a rose that was open for three days outdoors in the month of September at West Grove, Pennsylvania, U.S.A.:

*Color.*—Outer petal: outside surface—outer portion Phlox Pink, Plate 625/2, shading to Phlox Pink, Plate 625/3 toward middle of petal, with small area of Sulphur Yellow, Plate 1/3 at point of attachment; inside surface—outer portion Phlox Pink, Plate 625/2, shading to Neyron Rose, Plate 623/2 toward the center, with small area of Sulphur Yellow, Plate 1/3 at base. Inner petal: outside surface—outer surface Rose Bengal, Plate 25/3, shading to Phlox Pink, Plate 625/3 at center, with small area of Sulphur Yellow, Plate 1/3 at base; inside surface—outer surface Rose Pink, Plate 427/2, shading to Rose Pink, Plate 427/3 at center, and with small area of Sulphur Yellow, Plate 1/3 at point of attachment.

*General color effect.*—Newly opened flower—Rhodamine Pink, Plate 527/1 at outer edge of petals, shading to Rhodamine Pink, Plate 527/3 at center of flower. 3-days open—Rhodamine Pink, Plate 527/2 at outer edge of petals, shading to Rhodamine Pink, Plate 527/3 at center of flower.

*Behavior.*—Drop off cleanly; colors are heightened by cold weather.

*Flower longevity.*—On bush in garden—4 days in September. Cut roses grown outdoors and kept at living-room temperatures—3 days in September.

*Reproductive Organs*

Stamens: Many; arranged irregularly about pistils; mixed with petaloids.

Filaments: Many; most with anthers; medium length. Color—Sulphur Yellow, Plate 1.

Anthers: Open at various times; medium size. Color—Lemon Yellow, Plate 4.

Pollen: Abundant. Color—gold.

Pistils: Many.

Styles: Uneven; short; medium caliper; bunched.

Stigma: Color—yellow.

Ovaries: All enclosed in receptacle.

Hips: None observed at West Grove, Pennsylvania; rounded shape in France.

Sepals: Permanent; from medium to long in length; spear-shaped.

Seeds: None observed at West Grove, Pennsylvania; few seeds as observed in France.

*Plant*

Foliage:

*Leaves.*—Compound of 7 leaflets; abundant; medium size; moderately glossy.

*Leaflets.*—Shape—ovoid, with apex acute. Base—obtuse.

*Color.*—Mature: upper surface—Spinach Green, Plate 0960; under surface—Spinach Green, Plate 0960/2. Young: upper surface—Maroon, Plate 1030/1, shading to Lavender Green, Plate 000761/1 along center rib; under surface—Pansy Purple, Plate 928/1.

*Rachis (the supporting stem of the compound leaf).*—Medium caliper. Upper side—smooth. Under side—smooth.

*Stipules.*—From medium to long in length; narrow; with short points turning out at an angle of more than 45°.

*Disease resistance.*—Comparable to that of the average variety grown under the same cultural conditions at West Grove, Pennsylvania, U.S.A.

Growth:

*Habit.*—Climbing; much-branched.

*Growth.*—Vigorous.

*Canes.*—Heavy.

*Main stems.*—Color—near Lettuce Green, Plate 861. Prickles—few; color—Garnet Brown, Plate 00918. Hairs—none.

*Branches.*—Color—near Lettuce Green, Plate 861. Prickles—few; color—near Lettuce Green, Plate 861, overlaid with Erythrite Red, Plate 0027/2. Hairs—none.

*New shoots.*—Bright. Color—near Lettuce Green, Plate 861/2. Prickles—few; color—Erythrite Red, Plate 0027 at tip, shading to Erythrite Red, Plate 0027/1 at base. Hairs—none.

I claim:

A new and distinct variety of rose plant of the everblooming climber class, substantially as herein shown and described, characterized particularly as to novelty by the unique combination of a hardiness which is much superior to the average hardiness of everblooming roses in the middle Atlantic geographical area of the United States, excellent floriferousness, a remontance that is exceptional for a rose of the climber class, good self-cleaning characteristics evidenced by dropping of the flower petals cleanly before becoming unsightly with age, and a general color tonality of the flowers corresponding to Rhodamine Pink.

No references cited.